US011773049B2

(12) United States Patent
Kucmierczyk et al.

(10) Patent No.: US 11,773,049 B2
(45) Date of Patent: Oct. 3, 2023

(54) RU-CATALYZED DOMINO HYDROFORMYLATION/HYDROGENATION/ESTERIFICATION USING PHOSPHINE LIGANDS

(71) Applicant: EVONIK OPERATIONS GMBH, Essen (DE)

(72) Inventors: Peter Kucmierczyk, Herne (DE); Robert Franke, Marl (DE); Matthias Beller, Ostseebad Nienhagen (DE); Ricarda Dühren, Rostock (DE); Ralf Jackstell, Rostock (DE)

(73) Assignee: EVONIK OPERATIONS GMBH, Essen (DE)

( * ) Notice: Subject to any disclaimer, the term of this patent is extended or adjusted under 35 U.S.C. 154(b) by 56 days.

(21) Appl. No.: 17/530,629

(22) Filed: Nov. 19, 2021

(65) Prior Publication Data
US 2022/0162147 A1    May 26, 2022

(30) Foreign Application Priority Data

Nov. 23, 2020   (EP) .................................... 20209161

(51) Int. Cl.
| | | |
|---|---|---|
| *C07C 67/04* | (2006.01) | |
| *C07C 67/36* | (2006.01) | |
| *C07C 67/38* | (2006.01) | |
| *B01J 31/22* | (2006.01) | |

(52) U.S. Cl.
CPC ........... *C07C 67/04* (2013.01); *B01J 31/2234* (2013.01); *C07C 67/36* (2013.01); *C07C 67/38* (2013.01); *B01J 2231/321* (2013.01); *B01J 2231/645* (2013.01); *B01J 2531/821* (2013.01)

(58) Field of Classification Search
None
See application file for complete search history.

(56) References Cited

U.S. PATENT DOCUMENTS

| | | | |
|---|---|---|---|
| 3,168,553 A | | 2/1965 | Slaugh |
| 3,646,116 A | * | 2/1972 | McClure ................. C07C 67/38 |
| | | | 560/233 |
| 10,407,375 B2 | | 9/2019 | Sang et al. |
| 10,544,174 B2 | | 1/2020 | Dong et al. |

FOREIGN PATENT DOCUMENTS

| | | |
|---|---|---|
| EP | 0 329 252 B1 | 6/1992 |
| EP | 2 975 019 A1 | 1/2016 |
| EP | 3 272 732 A1 | 1/2018 |
| EP | 3 441 383 A1 | 2/2019 |

OTHER PUBLICATIONS

U.S. Appl. No. 17/530,620, filed Nov. 19, 2021, Kucmierczyk et al.
European Search Report dated May 17, 2021 for European Patent Application No. 20209161.7 (8 pages in German with Machine Translation).
Fleischer, I., et al. From Olefins to Alcohols: Efficient and Ragioselective Ruthenium-Catalyzed Domino Hydroformylation/Reduction Sequence. Angewandte Chemie International Edition. 2013. vol. 52, pp. 2949-2953.

* cited by examiner

*Primary Examiner* — Amy C Bonaparte
(74) *Attorney, Agent, or Firm* — Smith, Gambrell & Russell, LLP

(57) ABSTRACT

Ru-catalysed domino hydroformylation/hydrogenation/esterification using phosphine ligands.

15 Claims, No Drawings

RU-CATALYZED DOMINO HYDROFORMYLATION/HYDROGENATION/ ESTERIFICATION USING PHOSPHINE LIGANDS

The present invention relates to a Ru-catalysed domino hydroformylation/hydrogenation/esterification using phosphine ligands.

EP 0 329 252 B1 describes a process for producing carboxylic acids or esters. The process is catalysed through the use of a ruthenium compound in combination with an acidic compound. The acidic compound comprises one of the following elements: phosphorus, antimony, arsenic, molybdenum, tungsten.

I. Fleischer, K. M. Dyballa, R. Jennerjahn, R. Jackstell, R. Franke, A. Spannenberg, M. Beller, "From Olefins to Alcohols: Efficient and Regioselective Ruthenium-Catalyzed Domino Hydroformylation/Reduction Sequence", Angew. Chem. Int. Ed. 2013, 52, 2949-2953 describes a process for hydroformylation and subsequent reduction. The employed olefin is converted to the aldehyde and finally reduced to the alcohol.

The technical problem addressed by the present invention is that of providing a process which starting from an olefin results directly in an ester without isolation of intermediates. The original olefin is to form the alcohol part of the ester, i.e. the part bonded to the carbon atom of the C=O group via the oxygen. The alcohol part of the ester is moreover to have one more carbon than the employed olefin.

This problem is solved by a process according to Claim 1.
Process comprising the process steps of:
a) initially charging an ethylenically unsaturated compound;
b) adding a ligand of formula (I):

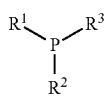
(I)

wherein
$R^1$, $R^2$, $R^3$ are selected from: $—(C_1\text{-}C_{12})$-alkyl, $—(C_6\text{-}C_{12})$-cycloalkyl, $—(C_6\text{-}C_{20})$-aryl, wherein the $—(C_6\text{-}C_{12})$-cycloalkyl radical and the $—(C_6\text{-}C_{20})$-aryl radical may have substituents which are selected from: $—(C_1\text{-}C_{12})$-alkyl, $—O—(C_1\text{-}C_{12})$-alkyl, $—SO_3Na$; and a compound comprising Ru;
c) adding an acid (II) having the formula (IIa) or (IIb):

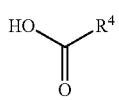
(IIa)

wherein $R^4$ is $—(C_1\text{-}C_{18})$-alkyl;

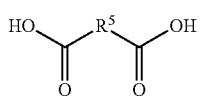
(IIb)

wherein $R^5$ is $—(C_1\text{-}C_{18})$-alkyl;
d1) feeding in CO;
e) heating the reaction mixture from a) to d) to convert the ethylenically unsaturated compound directly into an ester or diester of acid (II) without isolation of intermediates.

Step d) comprises process step d1) and optionally further process steps d2), d3) and d4).

In this process, process steps a), b), c) and d) can be effected in any desired sequence. Typically, however, the addition of CO is effected after the co-reactants have been initially charged in steps a) to c). Steps d) and e) can be effected simultaneously or successively. In addition, CO can also be fed in in two or more steps, in such a way that, for example, a portion of the CO is first fed in, then the mixture is heated, and then a further portion of the CO is fed in.

The expression $(C_1\text{-}C_{12})$-alkyl encompasses straight-chain and branched alkyl groups having 1 to 12 carbon atoms. Suitable $(C_1\text{-}C_{12})$-alkyl groups are especially methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The expression $(C_6\text{-}C_{12})$-cycloalkyl encompasses mono-, bi- or tricyclic hydrocarbyl groups.

The expression $(C_6\text{-}C_{20})$-aryl encompasses mono- or polycyclic aromatic hydrocarbyl radicals having 6 to 20 carbon atoms. These are preferably $(C_6\text{-}C_{14})$-aryl, more preferably $(C_6\text{-}C_{10})$-aryl.

Suitable $(C_6\text{-}C_{20})$-aryl groups are especially phenyl, naphthyl, indenyl, fluorenyl, anthracenyl, phenanthrenyl, naphthacenyl, chrysenyl, pyrenyl, coronenyl. Preferred $(C_6\text{-}C_{20})$-aryl groups are phenyl, naphthyl and anthracenyl.

The ethylenically unsaturated compounds used as reactant in the process according to the invention contain one or more carbon-carbon double bonds. These compounds are also referred to hereinafter as olefins for simplification. The double bonds may be terminal or internal. The ethylenically unsaturated compounds preferably have a carbon-carbon double bond.

Preference is given to ethylenically unsaturated compounds having 2 to 30 carbon atoms, preferably 2 to 22 carbon atoms, more preferably 2 to 12 carbon atoms.

In one embodiment, the ethylenically unsaturated compound is selected from: ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, 1-octene, 2-octene, di-n-butene, or mixtures thereof.

In one embodiment, $R^1$ is selected from: $—(C_1\text{-}C_{12})$-alkyl, $—(C_6\text{-}C_{20})$-aryl, $—(C_5\text{-}C_{20})$-heteroaryl.

In one embodiment, $R^1$, $R^2$, $R^3$ are selected from: $—(C_6\text{-}C_{12})$-cycloalkyl, $—(C_6\text{-}C_{20})$-aryl.

In one embodiment, $R^1$, $R^2$, $R^3$ are $—(C_6\text{-}C_{12})$-cycloalkyl.

In one embodiment, $R^1$, $R^2$, $R^3$ are $—Cy$.

In one embodiment, $R^1$, $R^2$, $R^3$ are $—(C_6\text{-}C_{20})$-aryl.

In one embodiment, $R^1$, $R^2$, $R^3$ are -Ph.

In one embodiment, $R^1$, $R^2$, $R^3$ are the same radical.

In one embodiment, the compound comprising Ru is selected from: $Ru_3(CO)_{12}$, $RuCl_3*H_2O$, $Ru(Cl)_2(DMSO)_4$, $Ru(acac)_3$.

In one embodiment, the compound comprising Ru is $Ru_3(CO)_{12}$.

In one embodiment, $R^4$ is —$(C_1-C_{12})$-alkyl.

In one embodiment, $R^4$ is —$(C_1-C_8)$-alkyl.

In one embodiment, $R^5$ is —$(C_1-C_{12})$-alkyl.

In one embodiment, $R^5$ is —$(C_1-C_8)$-alkyl.

In one embodiment, the process comprises the additional process step d2):

d2) feeding in $H_2$.

In one embodiment the $H_2$ pressure is in the range from 1 MPa (10 bar) to 6 MPa (60 bar).

In one embodiment, the process comprises the additional process step d3):

d3) adding $H_2O$.

In one embodiment, $H_2O$ is added in an amount such that the molar ratio of $H_2O$ to the ethylenically unsaturated compound is in the range from 1:1 to 10:1.

In one embodiment, the process comprises the additional process step d4):

d4) adding para-toluenesulfonic acid.

In one embodiment, the acid (II) is added in process step c) in an amount such that the molar ratio of acid to the ethylenically unsaturated compound is in the range from 2:1 to 10:1.

In one embodiment, the acid (II) has the formula (IIa).

In one embodiment, the acid (II) has the formula (IIb).

In one embodiment, the ligand in process step b) is selected from:

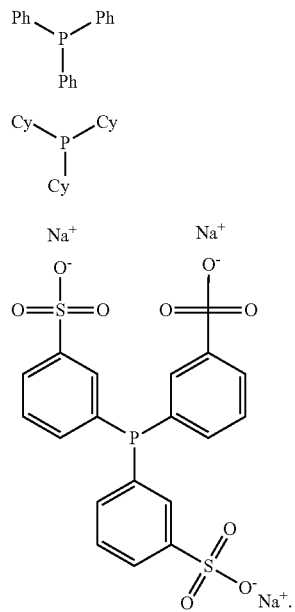

In one embodiment, the reaction mixture is in process step e) heated to a temperature between 50° C. and 180° C., preferably between 80° C. and 160° C., more preferably between 100° C. and 150° C., to convert the ethylenically unsaturated compound to the ester.

The invention is described in detail hereinafter by working examples.

General Procedural Methods

All operations with air- and moisture-sensitive substances were performed in an argon atmosphere and with baked-out glass apparatuses using Schlenk techniques. The chemicals were obtained from commercial producers and employed as supplied, provided purity was at least 98%. Oxygen-free and dry solvents were prepared by distillation under argon. Synthesis gas (CO-99.997%, $H_2$/CO:1:1+/−1%) was obtained from Linde.

The products were analysed by $^1$H-NMR and $^{13}$C-NMR spectroscopy. The NMR spectra were recorded on Bruker AV 400 (400 MHz), Bruker AV 300 (300 MHz) or Fourier 300 (MHz) instruments. Chemical shifts δ (ppm) are reported relative to the employed solvent: References for $CDCl_3$ were 7.26 ppm ($^1$H-NMR) and 77.16 ($^{13}$C-NMR). $^{13}$C-NMR spectra were recorded with a broadband decoupled method.

GC analyses were performed on a 7890A GC system from Agilent Technologies using a 30 m HP-5 column. The carrier gas employed was argon. The products were analysed by GC or GC-MS or isolated by column chromatography (silica, EtOAc/heptane). The GC yields were calculated by internal calibration. Hexadecane was used as an internal standard.

Performing the Catalytic Experiments

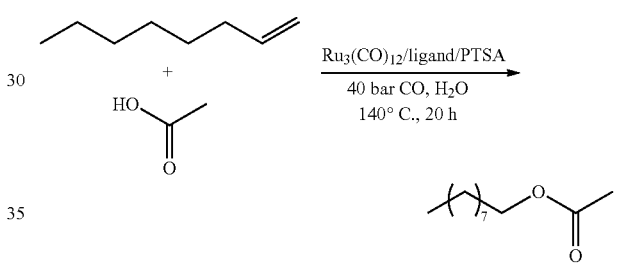

The catalytic experiments were performed in 4 mL glass vials having screwtop caps and a PTFE septum. The vials were provided with oven-dried magnetic stirrers and the connection to the gas atmosphere was made using a needle. The reaction batch comprised 2 mL. The vials were placed in a 300 mL Parr4560 autoclave and stirred using a magnetic stirrer. In the first step $Ru_3(CO)_{12}$ (5 mol %), ligand (5.5 mol %) and PTSA*$H_2O$ (20.6 mol %) are weighed into the vial. The vial is sealed with a screwtop cap provided with a septum, sealed and connected to the argon atmosphere via a cannula. The vial was evacuated three times and purged with argon. Acetic acid (1.17 mL), $H_2O$ (0.35 mL) and 1-octene (3 mmol) were injected by Hamilton syringe. The vial was transferred into the autoclave under an argon atmosphere. The autoclave is tightly sealed and initially purged three times with 10 bar of CO at room temperature. Subsequently, 40 bar of CO are applied, the autoclave is placed on a magnetic stirrer in an aluminium block and heated to 140° C. for 20 h. After 20 h, the autoclave was cooled to room temperature and the pressure was cautiously released. As internal standard 100 μL of hexadecane were introduced into the reaction solution. The yield was determined by GC analysis.

The reaction was performed under analogous conditions for the ligands (1) to (3) and for the comparative ligand (4). Since the comparative ligand (4) is a bidentate ligand only 2.75 mol % were employed instead of the 5.5 mol %. To obtain a constant molar ratio of PTSA*$H_2O$:L (3.75:1) the amount was then reduced to 10.3 mol %.

(4)

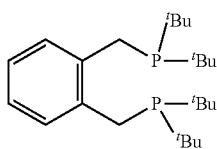

Reaction Conditions
  1-Octene: 3 mmol
  $Ru_3(CO)_{12}$: 5 mol % Ru
  Ligand (1) to (3): 5.5 mol % based on 1-octene
  Ligand (4): 2.75 mol % based on 1-octene
  $PTSA*H_2O$ using (1) to (3): 20.6 mol %
  $PTSA*H_2O$ using (4): 10.3 mol %
  $H_2O$:1-octene=6.5:1 (molar ratio)
  HOAc:1-octene=6.75:1 (molar ratio)
  CO pressure: 40 bar
  Temperature: 140° C.
  Reaction time: 20 h Experimental Results

| Ligand | Ester yield [%] |
|---|---|
| (1)* | 24 |
| (2)* | 25 |
| (3)* | 23 |
| (4) | 10 |

*inventive process

The invention claimed is:

1. A process comprising the process steps of:
  a) initially charging an ethylenically unsaturated compound;
  b) adding a ligand of formula (I):

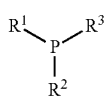

(I)

wherein
    $R^1$, $R^2$ and $R^3$ are selected from the group consisting of —$(C_1-C_{12})$-alkyl, —$(C_6-C_{12})$-cycloalkyl and —$(C_6-C_{20})$-aryl,
    wherein the —$(C_6-C_{12})$-cycloalkyl radical and the —$(C_6-C_{20})$-aryl radical may have substituents which are selected from the group consisting off —$(C_1-C_{12})$-alkyl, —O—$(C_1-C_{12})$-alkyl and —$SO_3Na$;
    and a compound comprising Ru;
  c) adding an acid (II) having the formula (IIa) or (IIb):

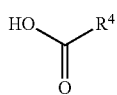

(IIa)

wherein $R^4$ is —$(C_1-C_{18})$-alkyl;

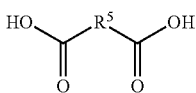

(IIb)

wherein $R^5$ is —$(C_1-C_{18})$-alkyl;
  d1) feeding in CO;
  e) heating a mixture formed from a) to d1) to convert the ethylenically unsaturated compound directly into an ester or diester of acid (II) without isolation of intermediates.

2. The process according to claim 1,
  wherein the ethylenically unsaturated compound is selected from: ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, 1-octene, 2-octene, di-n-butene, or mixtures thereof.

3. The process according to claim 1,
  wherein $R^1$, $R^2$ and $R^3$ are selected from the group consisting of —$(C_6-C_{12})$-cycloalkyl and —$(C_6-C_{20})$-aryl.

4. The process according to claim 1,
  wherein $R^1$, $R^2$ and $R^3$ are the same radical.

5. The process according to claim 1,
  wherein the compound comprising Ru is selected from the group consisting of $Ru_3(CO)_{12}$, $RuCl_3*H_2O$, $Ru(Cl)_2(DMSO)_4$ and $Ru(acac)_3$.

6. The process according to claim 1,
  wherein $R^4$ is —$(C_1-C_{12})$-alkyl.

7. The process according to claim 1,
  wherein $R^5$ is —$(C_1-C_{12})$-alkyl.

8. The process according to claim 1, where step d1) further comprises the additional process step d2):
  d2) feeding in $H_2$.

9. The process according to claim 8,
  wherein the $H_2$ pressure is in the range from 1 MPa to 6 MPa.

10. The process according to claim 1,
  where step d1) further comprises the additional process step d3):
  d3) adding $H_2O$.

11. The process according to claim 10,
  wherein $H_2O$ is added in an amount such that the molar ratio of $H_2O$ to the ethylenically unsaturated compound is in the range from 1:1 to 10:1.

12. The process according to claim 1,
  where step d1) further comprises the additional process step d4):
  d4) adding para-toluenesulfonic acid.

13. The process according to claim 1,
  wherein the acid (II) is added in process step c) in an amount such that the molar ratio of acid to the ethylenically unsaturated compound is in the range from 2:1 to 10:1.

14. The process according to claim 1,
  wherein the acid (II) has the formula (IIa).

15. The process according to claim 1, wherein the ligand in process step b) is selected from:
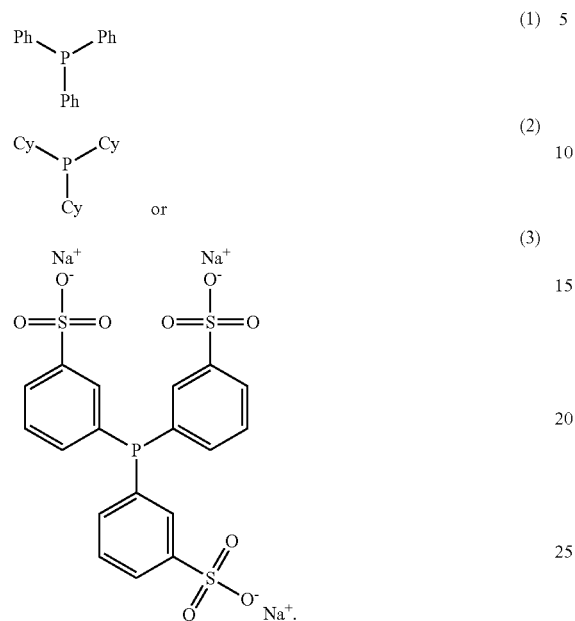
(1)
(2)
(3)
* * * * *

UNITED STATES PATENT AND TRADEMARK OFFICE
CERTIFICATE OF CORRECTION

PATENT NO. : 11,773,049 B2
APPLICATION NO. : 17/530629
DATED : October 3, 2023
INVENTOR(S) : Peter Kucmierczyk et al.

Page 1 of 1

It is certified that error appears in the above-identified patent and that said Letters Patent is hereby corrected as shown below:

On the Title Page

Item (72) add the inventor:
Carolin SCHNEIDER (Monheim am Rhein, DE).

Signed and Sealed this
Twenty-first Day of October, 2025

John A. Squires
*Director of the United States Patent and Trademark Office*